United States Patent
Sattler et al.

(10) Patent No.: US 10,346,733 B2
(45) Date of Patent: *Jul. 9, 2019

(54) ORIENTATION IDENTIFICATION LABEL, REAGENT CONTAINER CARRIER STRUCTURE, ANALYZER DEVICE AND READER MODULE

(71) Applicants: Roche Diagnostics Operations, Inc., Indianapolis, IN (US); Hitachi High-Technologies Corporation, Minato-ku (JP)

(72) Inventors: Stephan Sattler, Starnberg (DE); Yusuke Minemura, Ibaraki-ken (JP); Takuya Yamaguchi, Ibaraki-ken (JP)

(73) Assignees: ROCHE DIAGNOSTICS OPERATIONS, INC., Indianapolis, IN (US); HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/267,209

(22) Filed: Sep. 16, 2016

(65) Prior Publication Data
US 2017/0004394 A1    Jan. 5, 2017

Related U.S. Application Data

(63) Continuation of application No. 14/515,701, filed on Oct. 16, 2014, now Pat. No. 9,489,610, which is a (Continued)

(30) Foreign Application Priority Data

Jul. 27, 2007    (EP) .................................... 07014787

(51) Int. Cl.
*G08B 25/00*    (2006.01)
*G06K 19/077*    (2006.01)
(Continued)

(52) U.S. Cl.
CPC ........ *G06K 19/07703* (2013.01); *B01L 3/545* (2013.01); *G06K 19/0776* (2013.01);
(Continued)

(58) Field of Classification Search
CPC ............ C12Q 1/6827; C12Q 2563/143; C12Q 2565/633; C12Q 1/6825; C12Q 1/689;
(Continued)

(56) References Cited

U.S. PATENT DOCUMENTS 4,243,322 A    1/1981 Ingalz
4,264,327 A    4/1981 Blum
(Continued)

FOREIGN PATENT DOCUMENTS

EP    1 503 214 A2    2/2005
EP    1 707 268 A2    10/2006
(Continued)

*Primary Examiner* — Daniel Previl
(74) *Attorney, Agent, or Firm* — Woodard, Emhardt, Henry, Reeves & Wagner, LLP

(57) ABSTRACT

A reagent container carrier structure for holding at least one reagent container, wherein the carrier structure has thereon an RFID assembly and an optically detectable definition pattern defining an orientation of the carrier structure, is disclosed. The reagent container carrier structure may have an orientation identification label that has a front surface and a back surface, and further include an RFID assembly positioned on the back surface, and an optically detectable definition pattern defining an orientation of the label on the front surface. A reader module for reading RFID data in combination with optically detectable data defining an orientation of a respective label is also disclosed.

20 Claims, 7 Drawing Sheets

Related U.S. Application Data continuation of application No. 12/693,687, filed on Jan. 26, 2010, now Pat. No. 8,890,706, which is a continuation of application No. PCT/EP2008/006150, filed on Jul. 25, 2008.

(51) Int. Cl.
   *B01L 3/00* (2006.01)
   *G09F 3/10* (2006.01)
   *G01N 35/00* (2006.01)

(52) U.S. Cl.
   CPC . *G06K 19/07758* (2013.01); *G06K 19/07775* (2013.01); *G09F 3/10* (2013.01); *B01L 2300/022* (2013.01); *G01N 2035/00772* (2013.01)

(58) Field of Classification Search
   CPC .............................. C12Q 1/6895; C12Q 1/701; C12Q 2600/156; C12Q 1/6897; G01N 35/00732; G01N 1/30; G01N 1/312; G01N 1/36; G01N 24/08
   USPC ............ 340/686.1, 572.1–572.9, 568.1, 540, 340/539.1
   See application file for complete search history.

(56) References Cited

U.S. PATENT DOCUMENTS

| | | | |
|---|---|---|---|
| 4,775,638 A | 10/1988 | Haisma | |
| 5,354,654 A | 10/1994 | Ligler et al. | |
| 5,543,332 A | 8/1996 | Lihme et al. | |
| 5,649,081 A * | 7/1997 | Nakajima | G06T 19/20 345/419 |
| 5,936,527 A | 8/1999 | Isaacman et al. | |
| 7,562,025 B2 | 7/2009 | Mallett et al. | |
| 8,890,706 B2 * | 11/2014 | Sattler | B01L 3/545 340/539.1 |
| 2001/0013830 A1 * | 8/2001 | Garber | G06K 7/10079 340/572.4 |
| 2002/0012535 A1 | 1/2002 | Manico et al. | |
| 2002/0030598 A1 | 3/2002 | Dombrowski et al. | |
| 2003/0087446 A1 * | 5/2003 | Eggers | B01L 3/5085 436/48 |
| 2005/0186114 A1 * | 8/2005 | Reinhardt | B01L 9/52 422/65 |
| 2005/0205673 A1 * | 9/2005 | Morris | B01L 3/5027 235/385 |
| 2005/0226780 A1 | 10/2005 | Sandell et al. | |
| 2005/0286956 A1 | 12/2005 | Braun et al. | |
| 2006/0213964 A1 * | 9/2006 | Excoffier | B01L 3/5457 235/375 |
| 2006/0239867 A1 | 10/2006 | Schaeffer | |
| 2007/0013541 A1 | 1/2007 | Harazin et al. | |
| 2007/0139181 A1 | 6/2007 | Eren et al. | |
| 2008/0092646 A1 * | 4/2008 | Halaka | G01F 23/268 73/304 C |
| 2008/0214412 A1 * | 9/2008 | Stahler | B01J 19/0046 506/30 |
| 2009/0071829 A1 | 3/2009 | O'Banion et al. | |

FOREIGN PATENT DOCUMENTS

| | | |
|---|---|---|
| WO | WO 2005/111925 A1 | 11/2005 |
| WO | WO 2006/027054 A1 | 3/2006 |
| WO | WO 2007/007085 A2 | 1/2007 |

\* cited by examiner

ORIENTATION IDENTIFICATION LABEL, REAGENT CONTAINER CARRIER STRUCTURE, ANALYZER DEVICE AND READER MODULE

CROSS REFERENCE TO RELATED APPLICATIONS

This application is a continuation of U.S. application Ser. No. 14/515,701 filed Oct. 16, 2014, which is a continuation of U.S. application Ser. No. 12/693,687 filed Jan. 26, 2010, which is a continuation of International Application No. PCT/EP2008/006150 filed Jul. 25, 2008, which claims priority to EP Application No. 07014787.1, filed Jul. 27, 2007.

TECHNICAL FIELD

Embodiments of the present invention relate generally to RFID technology, and particularly to an orientation identification label using RFID technology, a reagent container carrier structure for holding at least one reagent container, also using RFID technology for storing, reading and writing information relating to the reagents held in the respective carrier structure as well as an analyzer device for analyzing chemical, biological or pharmaceutical work probes and a method to operate such an analyzer device.

BACKGROUND

Analyzer devices are important work tools and systems in laboratory analytics in the clinical area, chemical and pharmaceutical area, in immunology etc. Modern analyzer devices are conceived in a modular manner and provide for fully automated laboratory work. Different modules relate to different fields of analytics, using for example dispenser technology or pipette technology. Reagents used in the analytical work are usually provided in individual reagent containers, wherein one or more reagent containers are placed in a reagent container carrier structure. Reagent container carrier structures are well-known in this field of technology under various terms such as racks, cassettes, cartridges etc. For ease of reference, all these holding devices will be referred to as carrier structures or reagent container carrier structures throughout this application.

In the course of the analyzing process, one or more carrier structures holding each at least one reagent container are placed in a respective analyzer device. In order for the analyzer device to be able to treat the inserted carrier structure properly, i.e. identifying its content etc., each carrier structure usually comprises a barcode label on its outer surface. The analyzer device in turn comprises a barcode reader installed in such a manner that the barcode information contained on the label of the carrier structure can be read and transferred to a computing and control unit of the analyzer device.

With the introduction of RFID technology in laboratory work, particularly for identification of reagent work probes, RFID assemblies on test tubes and other reagent containers have become more and more widespread.

US 2006/0239867 A1 discloses specimen cassettes for laboratory samples including RFID tags that provide identifying information, such as accession and block numbers.

WO 2006/041482 A1 discloses an automatic blood analysis and identification process permitting patient identification and other vital information to be automatically printed directly on a container holding a sample of a body fluid sample almost immediately after the sample has been drawn and analyzed. There is no manual handling of the sample between the draw and the identification. The process for analyzing the body fluid includes placing the body fluid sample in a container which is placed in a fluid analyzing unit. The sample is analyzed to determine characteristics of the body fluid which are then transferred to the container. The system may utilize radio frequency identification technology to communicate electronic data bearing the information to an RFID inlet associated with the container.

US 2006/0213964 A1 discloses a sample container comprising an RFID tag positioned near the open end of the sample container, and further discloses a sample handling apparatus operating with one or more sample containers and including a robotic assembly for moving a sample probe device and a sample probe supported by a guide of the sample probe device.

US 2005/0205673 A1 discloses a biological reagent carrier device employing RFID technology to associate information with biological reagents. The carrier supports the biological reagent and at least one RFID tag including a carrier RFID antenna coupled to the carrier, wherein the RFID tag is operable to be read by an RFID reader, and the RFID tag can include identification, supplemental, and all rights information for the biological reagent.

SUMMARY

In contrast thereto, embodiments of the present invention provide an orientation identification label using RFID technology, a reagent container carrier structure for holding at least one reagent container, also using RFID technology for storing, reading and writing information relating to the reagents held in the respective carrier structure as well as an analyzer device for analyzing chemical, biological or pharmaceutical work probes and a method to operate such an analyzer device.

According to an embodiment of the invention, the orientation identification label comprises a front surface and a back surface as well as an RFID assembly positioned on the back surface and an optically detectable definition pattern defining an orientation of the label on the front surface. This allows detecting the physical orientation of any structure on which the orientation identification label according to the invention is applied. This is particularly suitable in connection with an automated optical detection device. The label may comprise, preferably on its back surface, an adhesive layer to allow easier application on any surface the label is to be applied.

The optically detectable definition pattern may comprise a geometrical design allowing identification of an orientation. Any geometrical design allowing to identify its orientation in an unequivocal manner can be used, such as, for example, a geometrical design which is asymmetric to at least one of the transversal or longitudinal axes of the label, or a geometrical design which is asymmetric to an axis of the design which is substantially perpendicular to the direction of orientation to be identified, and which, in either case, is not point-symmetric. In order to minimize false identifications of orientation, the geometrical design might be chosen to be as simple as possible and not too complex.

In an alternative embodiment, the optically detectable definition pattern according to the invention comprises at least two different colors allowing identification of an orientation. In the context of this application, the term "colors" is to be understood to also comprise black, white and grey. Thus, the least complex definition pattern according to the invention would be a label consisting of two adjacent rectangles, one of the rectangles been white and the other of the rectangles being black. However, other color combinations and/or combinations of more than two colors might be used. Again, in order to minimize risk of false detections, the patterns might be chosen not to be too complex. The definition pattern according to the invention might also comprise at least two different sub-patterns, such as, for example, a label consisting of two rectangular forms, the first rectangular form comprising a number of horizontal black lines on white ground, the second rectangular form comprising a number of vertical black lines on white ground.

In another embodiment of the invention, a reagent container carrier structure for holding at least one reagent container is provided, the carrier structure comprising thereon an RFID assembly and an optically detectable definition pattern according to the invention and as described above. The definition pattern on the carrier structure allows for an unequivocal identification of the orientation of the carrier structure which can be advantageous in case carrier structures are fed in a laboratory analyzer device, thus allowing determining whether one or more of the inserted carrier structures where inserted in the wrong direction.

The definition pattern according the invention and the RFID assembly can be applied to the carrier structure either separately (and possibly at different locations) or by means of the orientation identification label according to the invention and as described above.

In still another embodiment of the invention, a reader module is provided for reading RFID data in combination with optically detectable data defining a presence and an orientation of a respective label, both data being integrated in an orientation identification label which is to be attached to a reagent container carrier structure. The reader module comprises at least one RFID reader which is configured to detect the RFID data, and at least one optical element which is configured to detect the optically detectable data. It is also possible that the RFID data and the optically detectable data are provided on separate labels, respectively, wherein those separate labels in combination form the orientation identification label and can be, for example, adhered on top of each other to a corresponding reagent container carrier structure.

The reader module allows to detect the presence as well as the orientation of a respective label, i.e. the reader module allows to determine via a respective label which is attached, for example, to a reagent container carrier structure, whether the reagent container carrier structure is placed correctly within a corresponding conveyor system.

The reader module according to the invention can be used for reading the data of an orientation identification label according to the invention, namely the RFID assembly positioned on the back surface of the label, and the optically detectable definition pattern defining an orientation of the label on the front surface of the label.

The present description also covers a computer program with program coding means which are suitable for carrying out a process according to an embodiment of the invention as described above when the computer program is run on a computer or on a computing unit of an analyzer device, respectively. The computer program itself as well as stored on a computer-readable medium is claimed.

Further features and embodiments will become apparent from the description and the accompanying drawings.

It will be understood that the features mentioned above and those described hereinafter can be used not only in the combination specified but also in other combinations or on their own, without departing from the scope of the present disclosure.

Various implementations are schematically illustrated in the drawings and are hereinafter explained in detail with reference to the drawings. It is understood that both the foregoing general description and the following description of various embodiments are exemplary and explanatory only and are not meant to be restrictive or to be read into the claims. The accompanying drawings, which are incorporated in a constitutive part of this specification, illustrate some embodiments, and together with the description serve to explain the principles of the embodiments described herein.

DETAILED DESCRIPTION

Figure 1A:
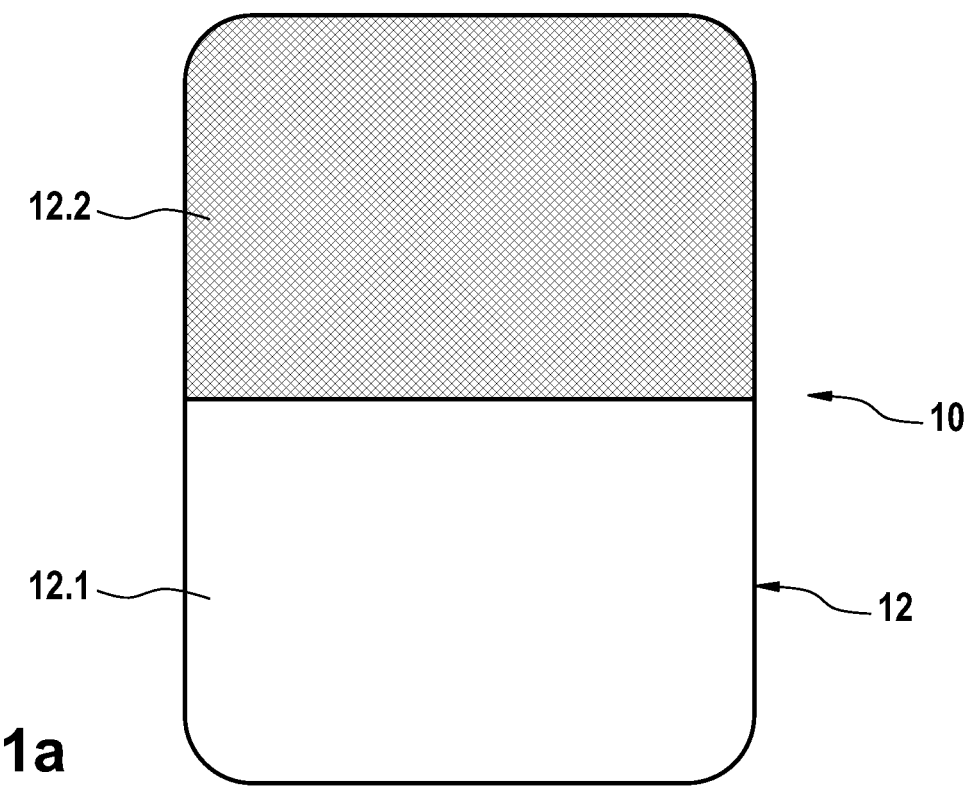
FIGS. 1a and 1b show the front surfaces of first and second embodiments, respectively, of an orientation identification label according to the invention.

Reference will now be made in detail to some embodiments, examples of which are illustrated in the accompanying drawings. Wherever possible, the same reference numbers are used throughout the drawings to refer to the same of like parts.

Radio Frequency Identification (RFID) provides a convenient mechanism for identifying and detecting objects using wireless electromagnetic signals. A basic RFID system has at least one RFID reader and at least one RFID assembly (the latter also known by the term "transponder" or "RFID tag"). Typically, RFID readers can include a coil or antenna and circuitry to transmit and receive signals with the coil or antenna. An RFID assembly or tag or transponder also includes a coil or antenna and some information stored on an RFID chip that can be read by an RFID reader.

The RFID reader antenna generates an electromagnetic field, thereby transferring energy to the tag. Depending on the design of the tag, a portion of the energy transferred to the tag will be reflected to the reader so as to provide information about the tag back to the reader. Some RFID systems can be used to read and optionally write data to and from the RFID tag. RFID readers can generate signals spanning distances from less than one centimeter to more than fifty meters depending on frequency and power of the signals generated at the RFID reader antenna.

Typically, RFID assemblies or tags are categorized as either active or passive. Active RFID tags are powered by an internal battery and are typically read/write, i.e. tag data can be rewritten and/or modified. An active tag's memory size varies according to application requirements, some systems operating with up to 1 MB of memory and more. Passive RFID tags operate without a separate external power source and obtain operating power generated from the reader. Passive tags are consequently typically lighter than active tags, less expensive, and offer a long operational lifetime. Passive tags typically have shorter read ranges than active tags and require a higher-powered reader. Read-only tags are typically passive and can be programmed with a unique set of data (usually 32 to 128 bits) that is typically predetermined at the time of manufacture of the tag. It is understood that passive read/write tags can also be employed consistent with the present teachings.

Consequently, the term "RFID assembly" or "RFID tag", respectively, as used herein refers to either an active or passive RFID tag that contains information. The RFID tag can be read only or read/write and the information associated with the RFID tag can be hard-coded into the RFID tag at the time of manufacture or at some later time, all the RFID tag can contain information that is written to the RFID tag throughout its lifetime.

The term "RFID reader" as used herein includes devices that can read information from and/or write information into an RFID tag.

The term "information" as used herein refers to data that can be stored electronically in the RFID tag and can be retrieved to be used as machine readable or human readable data for processing the reagent and/or reagent container carrier structure and/or can be written to the RFID tag during or after processing. It covers but is not restricted to such information as type of reagent, lot size, production date, production place, application data, system type suitability, use-by date, set point, control point, calibration data, analyzer device log data, date of first opening, used in which device, sampling data, carrier structure control data, etc.

The term "optical detection device" as used herein refers to any device that can read or detect optical structures or patterns, such as optical sensors or optical detectors or video sensors. Such optical detection devices are well-known in the art and are based, for example, on LDD technology or CCD technology, to name only two.

The term "optically detectable definition pattern" as used herein refers to any pattern which is able to define an orientation. The definition pattern may comprise or consist of geometrical structures, such as an arrow, or a combination of circles, rectangles, squares and/or other basic geometrical structures. The pattern can, either alternatively or accumulatively, comprise or consist of various colors and/or color combinations. However, it is recommended the pattern not to be too complex in order to minimize, on the one side, the risks for false readings by the optical detection device and, on the other side, to ensure the pattern to be properly identifiable by a human operator.

The term "reagent" as used herein refers to any kind of reagent being used in containers in laboratory analyzer devices, such as dilutions, pre-treatment reagents, carry-over reagents, cleaning reagents, calibrators, reference solutions, or even patient samples.

FIG. 1a shows a top elevational view on a front surface 12 of a first embodiment of an orientation identification label 10 according to the present invention. The front surface 12 of the orientation identification label 10 comprises an optically detectable definition pattern consisting of a first portion 12.1 of the front surface 12 being white and a second portion 12.2 of the front surface being black (the black color of this second portion 12.2 being shown by cross-hatching in all Figures). The first and second portions 12.1 and 12.2 of the front surface 12 are of approximately the same size. Any appropriate material can be used for realizing orientation identification label 10 according to the invention. Materials for the label 10 might comprise paper, metal foil, polyethylene (PE), polypropylene (PP), polyester (PET), acetates etc. The person skilled in the art of label technology will find the appropriate material which is resistant enough for the laboratory environment and/or has the appropriate surface characteristics for a proper recognition by the optical detection device.

Figure 1B:
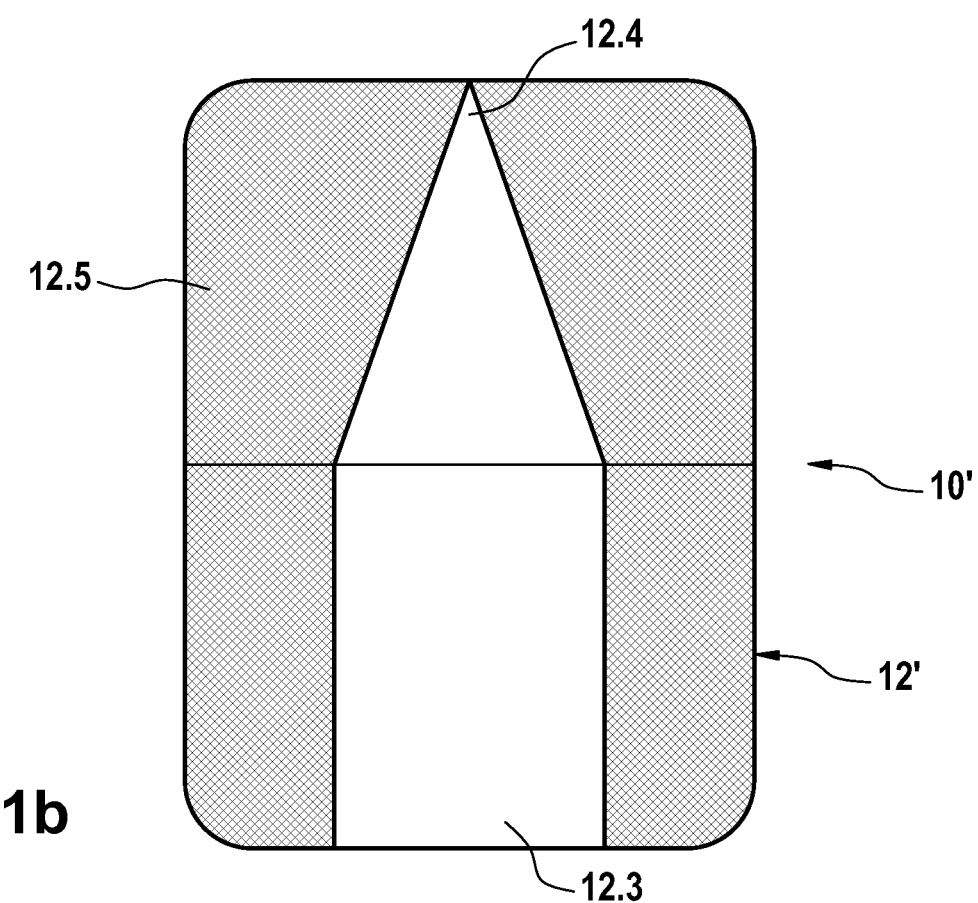

FIG. 1b shows a second embodiment of a front surface 12' of an orientation identification label 10' according to the present invention. In the second embodiment, the front surface also shows an optically detectable definition pattern which is also held in black and white and consists of a white rectangle 12.3 and a white triangle 12.4, the triangle 12.4 being arranged at directly adjacent to the rectangle 12.3. The remaining area 12.5 of the front surface 12' of the label 10' is in black (again indicated by cross-hatching). Thus, the pattern 12.3, 12.4, 12.5 gives the impression of a schematic drawing of a white house having a pointed roof or a white arrow-like configuration on black background.

The optically detectable definition pattern of the invention is, of course, not limited to patterns in black and white. It is also possible to use other colors, such as for example corporate colors of the manufacturer, provided that the chosen colors are contrastive enough to each other in order to be properly identifiable by an optical detection device, as explained in more detail below. The pattern is not intended to comprise any information beyond the orientation, and is intended to consist of simple geometrical configurations in contrastive colors. However, there might be manufacturers who, beyond using their corporate colors, also wish to include their corporate or trade logo which is feasible as long as optical detectability of the pattern is not affected.

Figure 2:
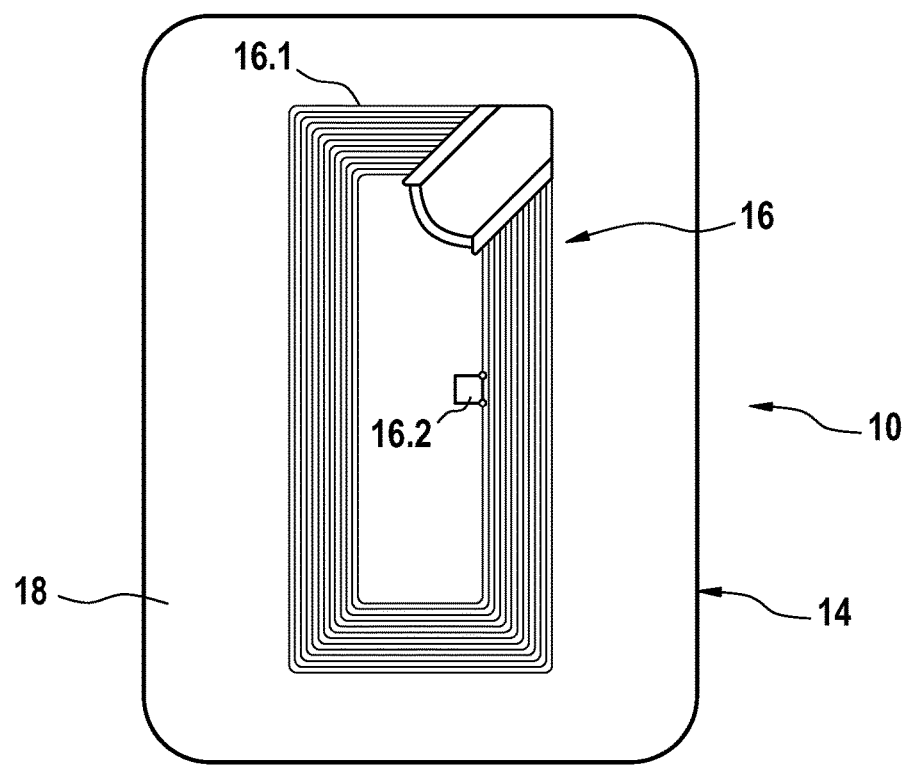
FIG. 2 shows the back surface of an embodiment of an orientation identification label according to the invention.

FIG. 2 shows a back surface 14 of the orientation identification label 10 according to the present invention. As can be seen from the highly schematic illustration of FIG. 2, an RFID assembly 16 is positioned on the back surface 14 of the label 10. The RFID assembly as such is well-known in the art and is also known as a "transponder" or "RFID tag". The RFID assembly 16 comprises an antenna or coil 16.1 and an RFID chip 16.2. The antenna 16.1 is the coupling element for establishing a communication contact with an appropriate RFID reader or RFID communication device as explained in more detail below.

Figure 3:
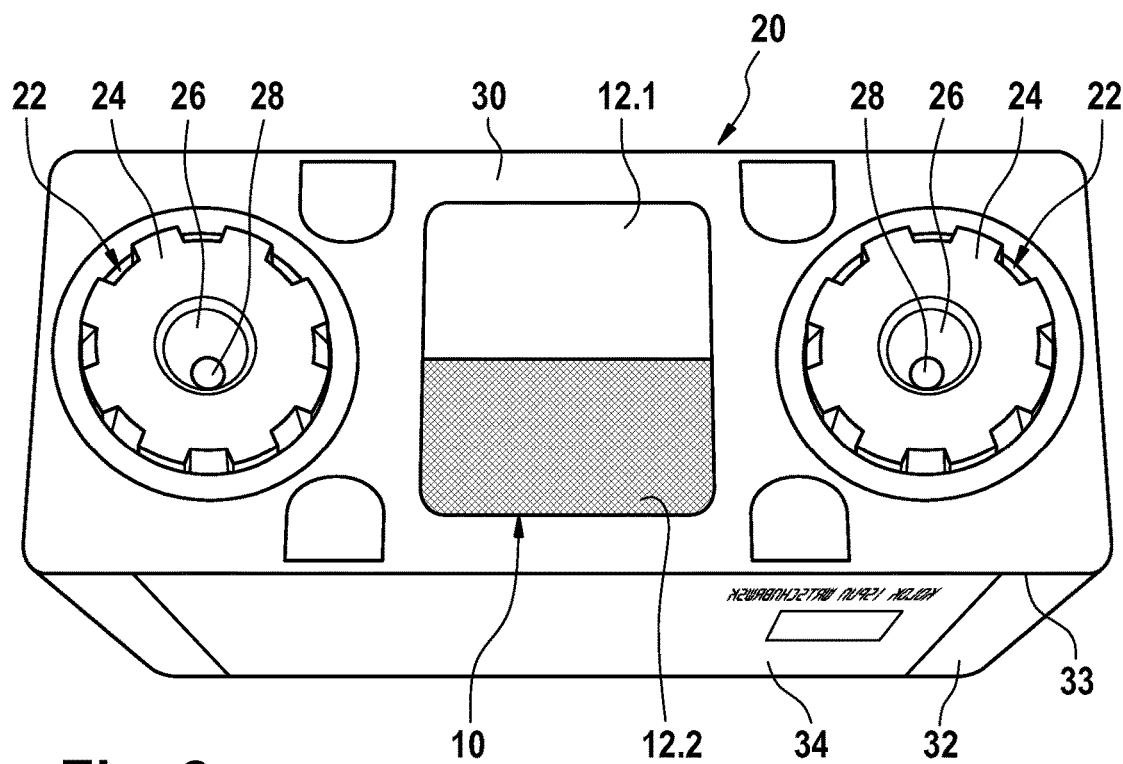
FIG. 3 shows a perspective view from above on a first embodiment of a reagent container carrier structure according to the invention.

FIG. 3 shows a reagent container carrier structure 20. The carrier structure 20 according to the illustrative embodiment holds two reagent containers 22 from which the respective (rotary or turn) caps 24 can be seen only in the perspective elevational view of FIG. 3. Each of the caps 24 comprises a centrical recess 26 with, at its bottom, an aperture destined to be penetrated by a pipetting probe, the aperture being covered by a membrane-like member 28 to be pierced by the probe.

The carrier structure 20 has substantially a cuboid form with the reagent containers 22 being placed into the carrier structure from above in corresponding cavities formed in the top surface 30 of the carrier structure 20.

On the top surface 30 and on an area between the two reagent containers 22, an orientation identification label 10 according to the invention is applied. The label 10 corresponds to the label embodiment as shown in FIG. 1a, particularly comprising the optically detectable definition pattern 12.1, 12.2 as already explained with reference to FIG. 1a.

In the illustration of FIG. 3, the black portion 12.2 of the definition pattern shows toward the bottom of the drawing whereas the white portion 12.1 of the pattern is oriented to the top of the drawing. On a side surface 32 of the carrier structure 20 adjacent to the black portion 12.2 of the definition pattern of the label 10, an additional label 34 comprising manufacturer information is applied.

According to one embodiment (not shown in detail in the drawings), it could be possible to combine the two labels 10, 34 by integrating the orientation identification label 10 with the product label 34 in such a manner that the product or manufacturer information would be applied on the side surface 32 with the orientation identification portion extending around the edge 33 between the side surface 32 and the top surface 30 of the carrier structure 20 and being applied to the top surface 30.

In the embodiment shown in FIG. 3, the RFID assembly 16 is attached to the back surface 14 of the orientation identification label 10 (as illustrated in FIG. 2). The application of the label can be performed by any known means, for example by means of an adhesive layer 18 applied to the back surface 14 of the label 10. However, it is also possible and within the scope of this invention to apply the optically detectable definition pattern, on the one side, and the RFID assembly, on the other side, separately from each other to the reagent container carrier structure 20. For example, it might be possible to attach the RFID assembly on a side surface of the reagent container carrier structure, and to attach the definition pattern on the top surface (as shown) or alternatively on the bottom surface (which would imply an optical detection device detecting/reading from below. One further possibility for a location of the RFID assembly is to attach the RFID assembly on the side surface of the carrier structure adjacent to the edge between the side surface and the top surface or even around one of the edges of the carrier structure (cf. FIG. 9). This would allow the RFID assembly to be read by an RFID reader positioned sideways of the carrier structure (when the same is inserted into the analyzer device through an inserting duct) as well as by an RFID reader positioned on top of the carrier structure (when the same is being conveyed, e.g. in a rotor as explained in more detail below). Of course, it would also be possible to attach the orientation identification label according to the invention at different location on the carrier structure, such as for example the bottom surface or one of the side surfaces or the front or even end surface. Moreover, it would be possible to provide the RFID assembly on a first label, and the optically detectable definition pattern on a second label, and to adhere the two labels on top of each other to the reagent container carrier structure.

The orientation identification label 10 allows that the orientation of a reagent container carrier structure 20 the label 10 is applied on can be determined in an unequivocal manner. If the carrier structure 20 is placed into a holder or retainer of an analyzer device, it might be fatal for the subsequently performed tests if the carrier structure 20 is placed into the analyzer device in a wrong direction which would lead to the wrong reagents being used. As the RFID assembly 16 on the carrier structure 20 does not allow determining an orientation of the carrier structure 20, there would be no possibility anymore to determine the orientation of the carrier structure 20 once placed into the analyzer device.

Figure 4:
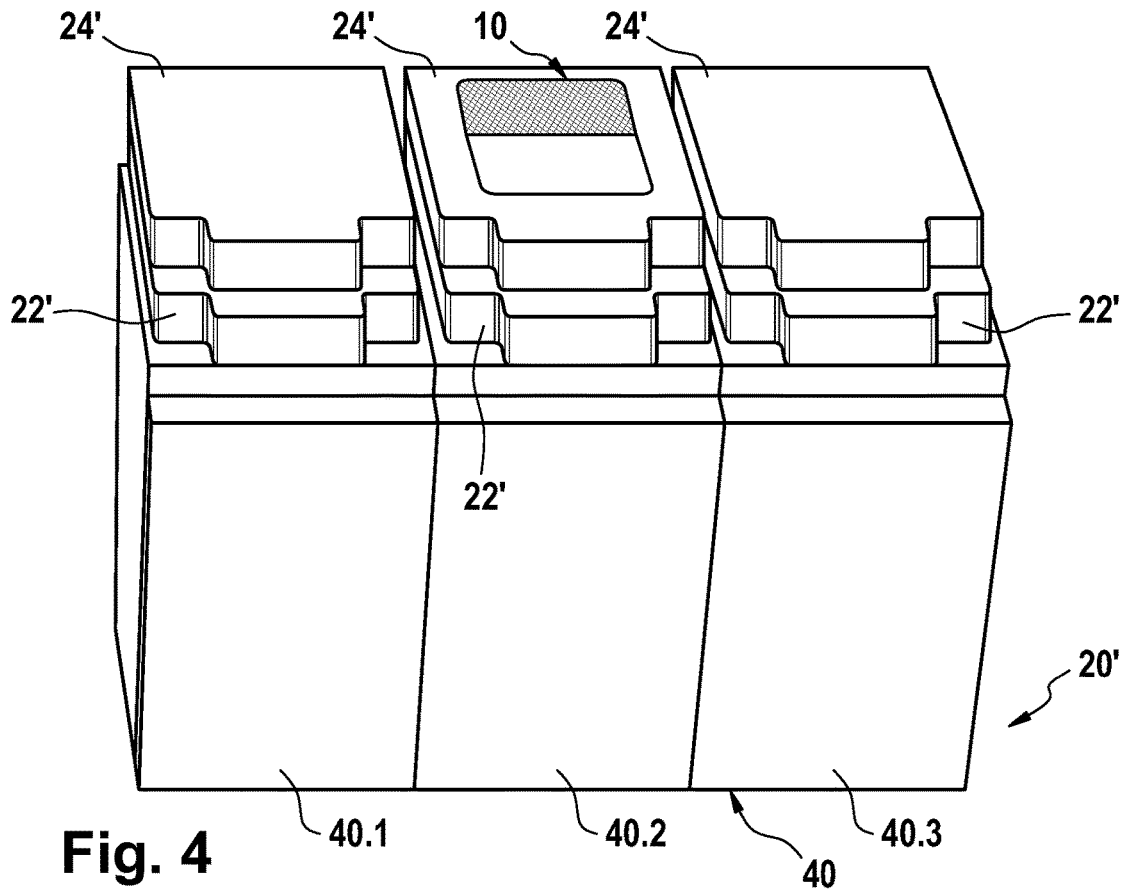
FIG. 4 shows a perspective view from above on a second embodiment of a reagent container carrier structure according to the invention.

FIG. 4 shows an alternative embodiment of a reagent container carrier structure 20' according to the present invention. The carrier structure 20' of FIG. 4 consists of a body 40 divided into three compartments 40.1, 40.2, 40.3 with a reagent container 22' being placed from the top into each compartment, respectively. The reagent containers 22' are closed by means of hinged caps 24'. As there is no void space available on the carrier structure 20' of FIG. 4 to apply an orientation identification label 10 according to the invention, the orientation identification label 10 is applied on one of the hinged caps 24', as can be seen from FIG. 4. In the example of FIG. 4, the label 10 is applied on top of the middle cap. However, it could also be applied on either one of the neighboring caps as long as it can be read by the corresponding optical detection device of the analyzer device.

Figure 9:
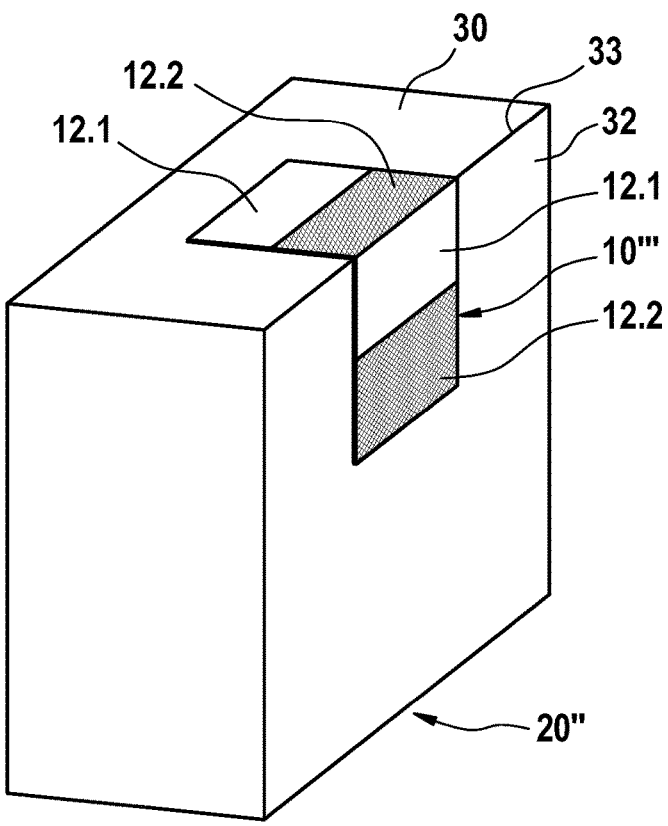
FIG. 9 shows in highly schematic manner a third embodiment of a reagent container carrier structure with an alternative location of the orientation identification label of the invention.

FIG. 9 shows a third embodiment of a reagent container carrier structure 20" according to the invention. The container carrier structure 20" shown in FIG. 9 is illustrated in highly schematic manner, leaving out details that have been shown and explained in detail with reference to FIG. 3. The container carrier structure 20" of FIG. 9 is very similar in appearance to the container carrier structure 20 of FIG. 3. The depiction of FIG. 9 illustrates an alternative manner of applying the orientation identification label according to the present invention, namely around an edge 33 between two (or three) surfaces of the carrier structure. This would allow, as already outlined above, to read the label optically and/or electronically from two directions with regard to the carrier structure. In the example of FIG. 9, these are the directions from above the top surface 30 of the carrier structure 20" and from sideways of a side surface 32 thereof. The orientation identification label 10''' applied around one of the upper edges 33 of the carrier structure 20" has—compared to the label 10 of FIG. 1a—a double pattern consisting of two white portions 12.1 and two black portions 12.2, alternating respectively, with two of the portions being located on the top surface 30 and with the respective remaining two portions being located on the side surface 32. This allows an optical detection of the orientation of the carrier structure 20" from above and/or from sideways. The RFID assembly on the back surface of the label 10''' extending around the edge 33 is thus connectable and readable from both directions, and one RFID reader positioned in the vicinity of the edge from either direction and within receiving distance (depending on the field strength) can read the RFID information. This leads to carrier structures having the capability to be employed with different types of analyzer devices (different so-called families of devices) in which the readers and/or detectors are located at different positions.

Figure 8:
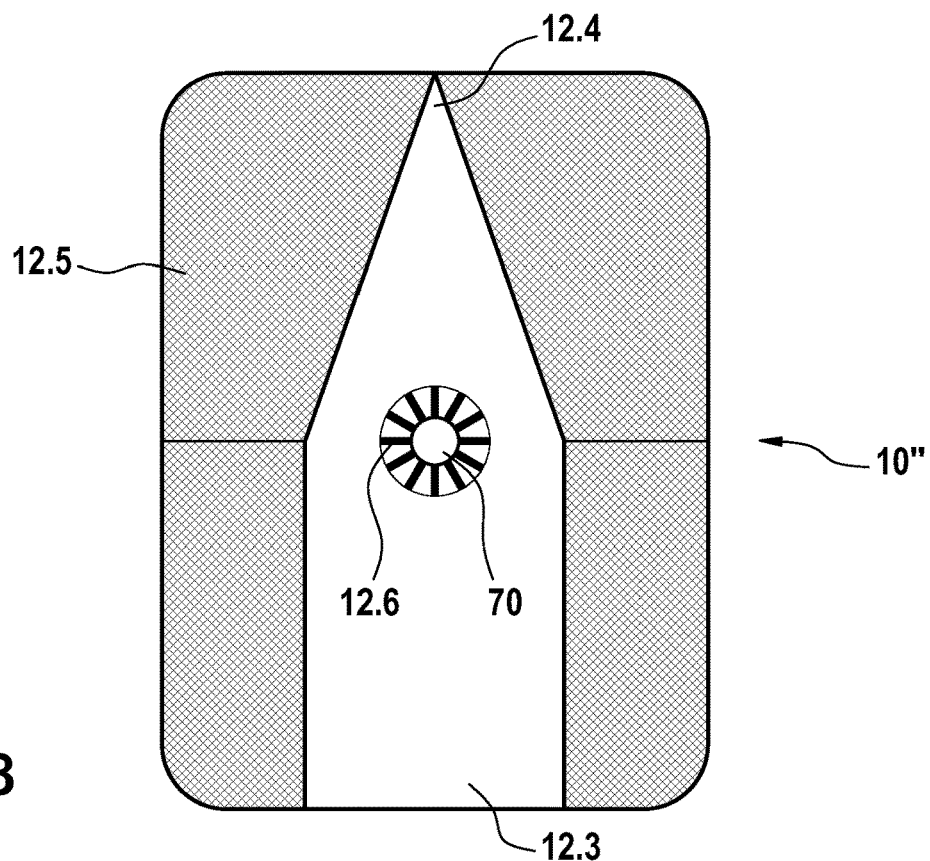
FIG. 8 shows the front surface of a third embodiment of an orientation identification label according to the invention.

There might be cases in which the orientation identification label is applied on a cap closing a reagent container (such as illustrated in FIG. 4) and in which the cap comprises an aperture for penetration by a pipetting probe element (such as the caps in the embodiment of FIG. 3). In such cases, the orientation identification label would cover the aperture, hampering easy access of the pipetting probe element to the cap's aperture. Therefore, the orientation identification label according to the invention might comprise an aperture for easy access of the pipetting probe element through the aperture of the label to the aperture in the reagent container cap. An example for an embodiment of such a label 10" is shown in FIG. 8. The label shown in FIG. 8 corresponds generally to the label of FIG. 1b, i.e. the label illustrated in FIG. 8 comprises the same basic pattern 12.3, 12.4, 12.5 as the label of FIG. 1b. In contrast to the label of FIG. 1b, the label of FIG. 8 further comprises a central aperture 70 of an appropriate diameter so that a pipetting probe element can penetrate and pass the label 10" smoothly. The label 10" is applied on the cap of a reagent container in such a manner that the aperture 70 of the label 10" is substantially concentric to and aligned with a corresponding aperture of the cap. The label 10" might comprise an additional optically detectable pattern 12.6 for identification of the aperture 70. In the embodiment of FIG. 8, the additional optically detectable pattern 12.6 is a concentric ring around aperture 70 comprising a number of fat radial lines. This enables the aperture 70 to be detected by an optical detection device, thus assisting in the precise alignment of the pipetting probe element in concentric manner to the aperture 70. However, any other suitable pattern identifying the aperture is possible. In a further embodiment (not shown in detail), the aperture 70 might only be created at the moment when the pipetting probe element pierces label 10" at the location identified by the additional optically detectable pattern 12.6.

Figure 5:
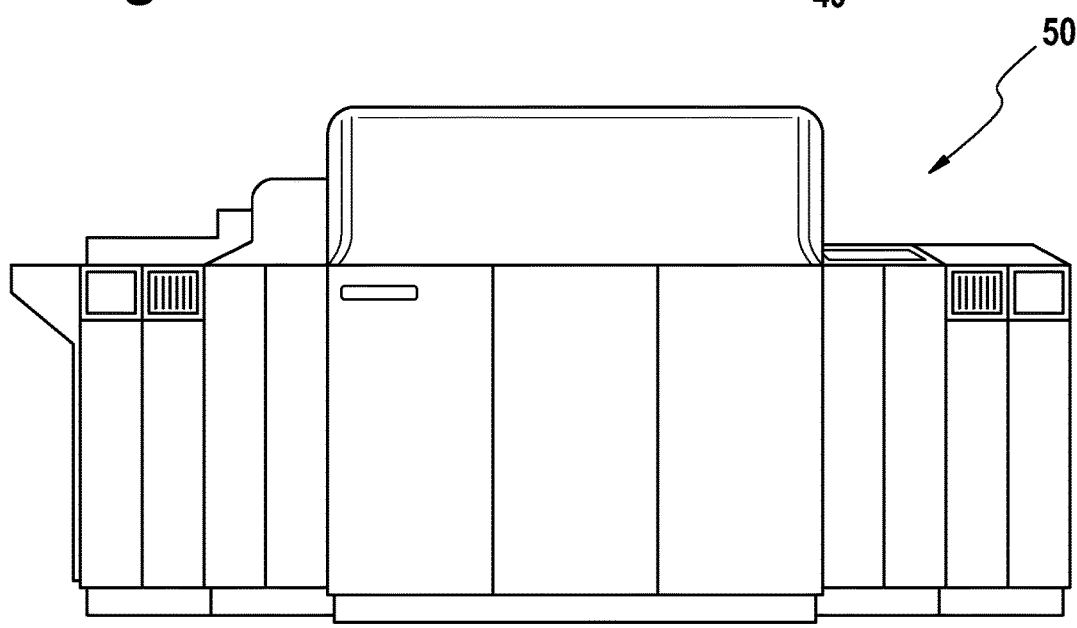
FIG. 5 shows, in a general view, an embodiment of an analyzer device according to the invention.

FIG. 5 shows an analyzer device for analyzing chemical, biological or pharmaceutical work probes. Such analyzer devices are well-known in the art and are commonly used in modern automated laboratory work. They are, for example, commonly found in clinical laboratory work places. Examples for such analyzer devices are the Elecsys® and the Cobas® systems from Roche Diagnostics, one of the applicants of the present invention.

Modern analyzer devices comprise conveyor systems for conveying the reagent containers or reagent container carrier structures, respectively, placed into the analyzer device. One possible embodiment for such a conveyor system is a rotational conveyor system 52 as partly shown in respective elevational view of FIG. 6. It is to be understood that the term "conveyor system" covers any system or assembly being able to convey or transport reagent containers or reagent container carrier structures, such as rotational or linear conveyors, belt or chain conveyors, or robotic assemblies.

The rotational conveyor system 52 comprises a rotor 54 rotating about a rotational axis 56. The rotor 54 comprises compartments 58 destined to hold reagent container carrier structures 20 (according to the embodiment shown in FIG. 3) in a radial manner. The reagent container carrier structures 20 placed into respective compartments 58 of the rotor 54 each comprise an optically detectable definition pattern on their respective top surfaces, with the respective black portion 12.2 of each of the patterns showing in counter clockwise direction of the rotor and the respective white portions 12.1 showing in clockwise direction of the rotor.

Figure 7:
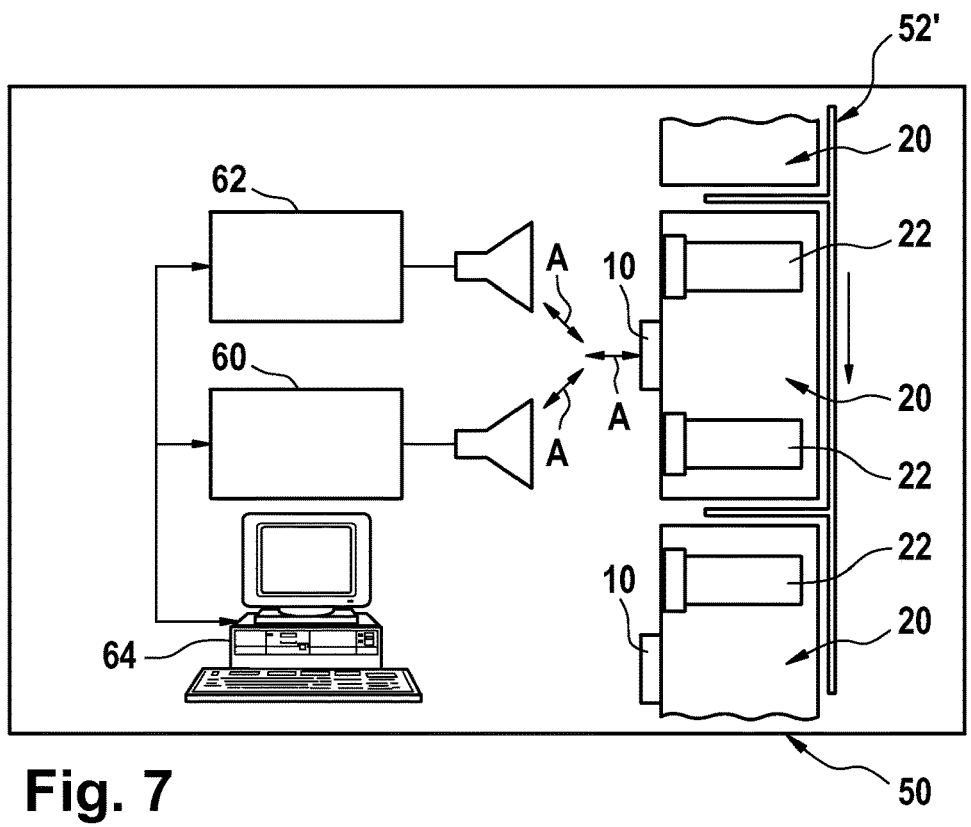
FIG. 7 shows in highly schematic manner an exemplary embodiment of the design of an analyzer device according to the invention comprising an RFID communication device and an optical detection device.

FIG. 7 shows a schematic view how the analyzer device 50 is built up. The analyzer device 50 comprises a conveyor system (which in FIG. 7 is, for the sake of clarity only, shown as a linear conveyor system 52'). The analyzer device 50 further comprises an RFID communication device 60 and an optical detection device 62. The analyzer device 50 also comprises a computing device 64 which can be made separately from the analyzer device (stand alone computer), or can be fully or partly integrated into the analyzer device. Computing device 64 can also serve as controlling unit for the analyzer device.

The RFID communication device 60 is destined to communicate with the RFID assembly 16 attached to the reagent container carrier structure, and the optical detection device 62 is destined to optically detect the optically detectable definition pattern on the reagent container carrier structure. As can be seen from FIG. 7, each of the carrier structures 20 loaded into the conveyor system 52' comprise, on their top surfaces 30, respectively, an orientation identification label 10 according to the invention. The identification label 10 comprises, as outlined with reference to FIGS. 1a, 1b and 2, on its front surface 12 an optically detectable definition pattern according to the invention, and on its back surface 14 an RFID assembly 16. Coupling between the RFID communication device 60 and the RFID assembly 16 is established by means well-known in the art and is therefore not further explained in detail here.

The optical detection device 62 is arranged to be able to optically detect any optically detectable definition pattern crossing its field of detection (optical measuring field). The optical detection itself is also well-known in the art and is therefore not further explained in detail here.

The signals detected and retrieved by the RFID communication device 60 and the optical detection device 62 are fed into the computing device 64 which evaluates the optical detection data received from the optical detection device and determines whether the orientation of the at least one carrier structure 20 in the conveyor system is correct.

In case the orientation of a carrier structure 20 is found to be correct, the further processing may continue. However, if the orientation of one (or more) carrier structures is found to be false, appropriate measures are to be taken. Appropriate measures can include interrupting the analyzing process and/or to generate and emit (output) an alarm and/or output an indication (to an operator) which carrier structure is wrongly oriented and/or to reorient automatically any wrongly oriented carrier structure.

A further alternative or accumulative measure might be to eject any wrongly oriented carrier structure automatically for correct reinsertion by an operator.

Figure 6:
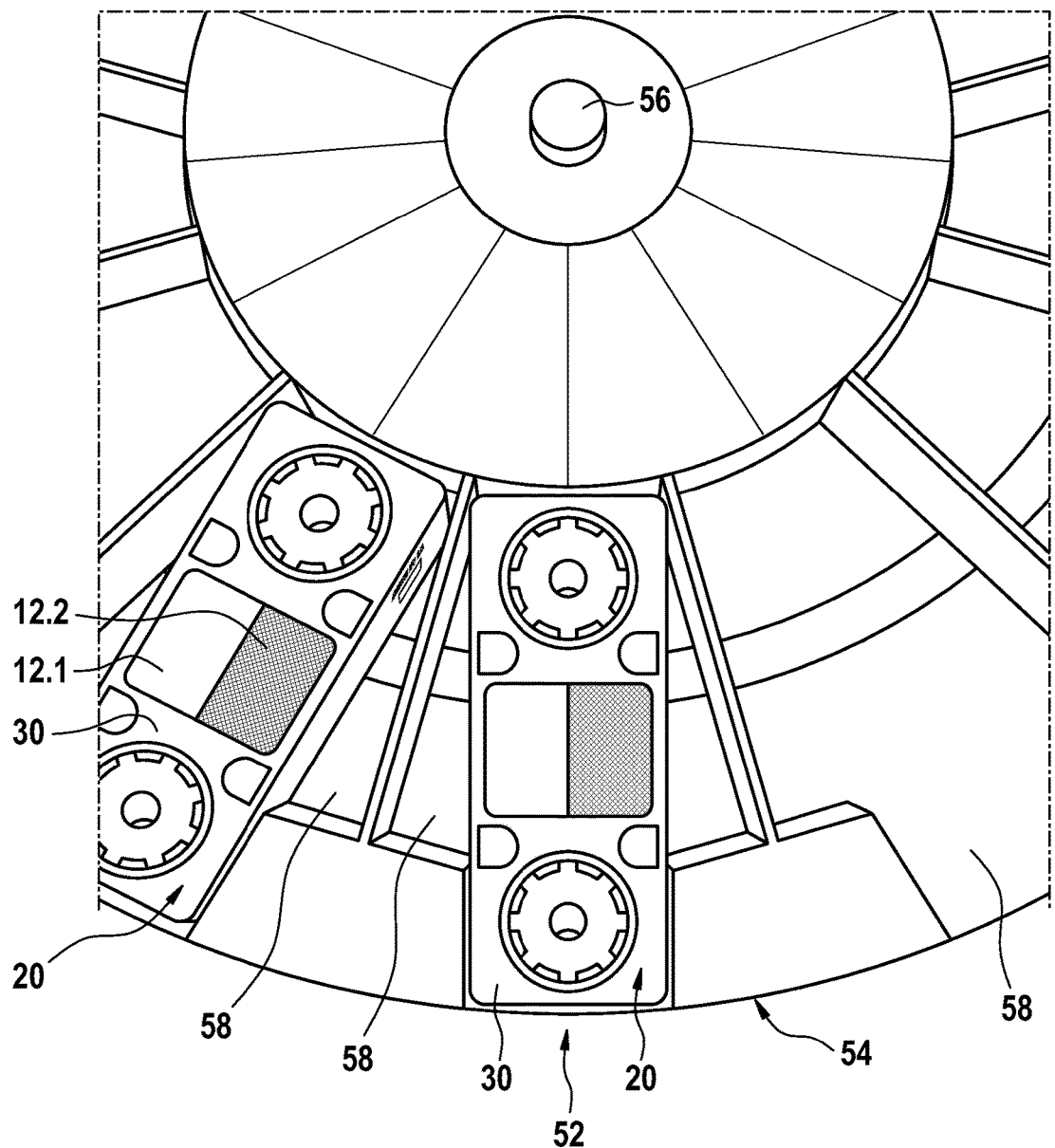
FIG. 6 shows, in a perspective view from above, an exemplary rotary conveyor system of an analyzer device for analyzing chemical, biological or pharmaceutical work probes with reagent container carrier structures according to the invention placed therein.

According to one possible embodiment of the invention, it might be appropriate to scan all carrier structures having been inserted into the analyzer device first, thus determining whether all carrier structures are placed into the analyzer device correctly, and only continue with the analyzing process if all the carrier structures have been found to be properly oriented. This method of proceeding is particularly appropriate in connection with analyzer devices in which a plurality of carrier structures can be inserted at one time, such as, for example, analyzer devices with rotational conveyor systems as illustrated in FIG. 6.

It might further be useful to not only scan the inserted carrier structures for their proper orientation by optically detecting the definition patterns on the respective carrier structures, but also scan, at the same time or subsequently, operability of the respective RFID assemblies. This can be done by establishing a test-connection (or test-coupling)

between the RFID communication device 60 and the respective RFID assemblies 16 when they pass the measuring field of the RFID communication device. It is possible to place the RFID communication device and the optical detection device next to each other so that their respective measuring fields overlap and they are thus able to read and detect the RFID assembly and the definition pattern of one given carrier structure simultaneously (as indicated by arrows A in FIG. 7). It might prove advantageous to provide a combined RFID reader/optical sensor for this purpose.

Scanning of the RFID assemblies before entering the analyzing process has the advantage that defective or faulty RFID chip can be determined beforehand and the carrier structure can be removed immediately and replaced by another one. In this case, it seems appropriate to have the analyzer device eject automatically a carrier structure whose RFID chip has failed.

The optical detection device 62 can also determine whether a carrier structure is inserted or not, i.e. whether a compartment in the conveyor system is empty or not. Alternatively, an additional optical detection device can be provided to detect presence of carrier structures independently of the detection of the orientation definition patterns.

Figure 10:
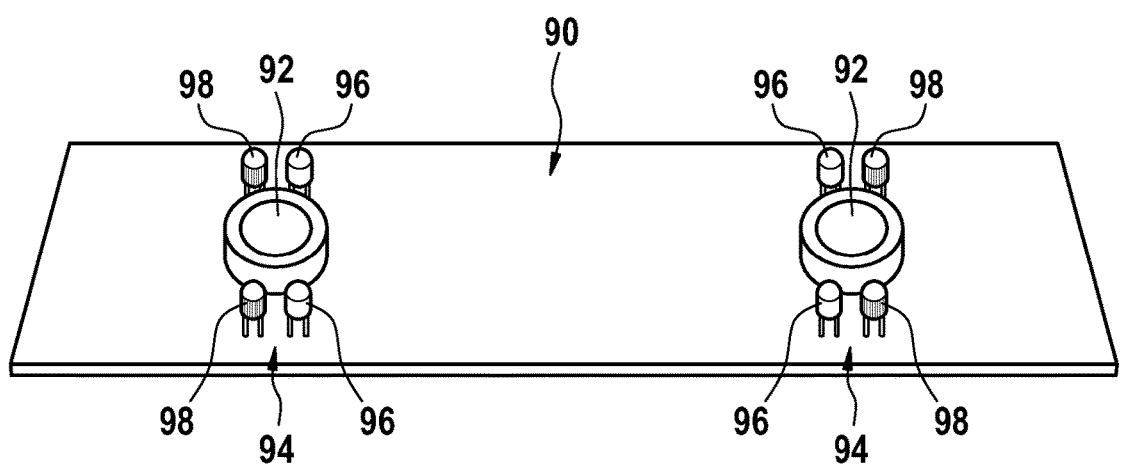
FIG. 10 shows an embodiment of a reader module according to the invention.

FIG. 10 shows an embodiment of a reader module 90, the reader module 90 comprising two RFID readers 92 and four optical elements 94. Each optical element 94 comprises a sender unit 96 and a receiver unit 98. The RFID readers 92 can include a coil or antenna and circuitry to transmit and receive signals (data) with the coil or antenna. Two optical elements 94, i.e. two pairs of sender and receiver units, are arranged symmetrically to each other with respect to one RFID reader 92, respectively. The receiver unit can be a conventional optical sensor. The sender unit is a light source. Alternatively, it would also be possible to provide a general diffuse light source replacing the respective single sender units. Via the RFID readers 92, it is possible to read RFID data which are integrated in a label, as, for example, a RFID assembly attached to an orientation identification label as shown in FIG. 2. The optical elements 94, two of which being arranged symmetrically to each other relating to one of the two RFID readers 92, respectively, are configured to optically detect optically detectable data on a respective label, such as, for example, an optically detectable definition pattern on a respective orientation identification label as shown in FIG. 1. As can be seen from FIG. 10, each of the two RFID readers 92 can be locally assigned to a pair of optical elements 94, the pair of optical elements 94 being symmetrically arranged with respect to the respective RFID reader 92. The reader module 90 as shown in FIG. 10 can be used to read two labels, each label being attached to one of two reagent container carrier structures, which in turn are conveyed, e.g. in a so-called two-lane reagent rotor. The reader module 90 can be fixedly mounted on top of such a reagent rotor, which comprises compartments destined to hold reagent container carrier structures in a radial manner as shown, for example, in FIG. 6. It is possible that the reagent, rotor comprises an inner lane and an outer lane, each lane comprising compartments destined to hold reagent container carrier structures. It is possible that the rotor positions are pre-defined, and that the rotor is clocked in preprogrammed steps. At each rotor stop, the reader module 90 is able to read the RFID data and the optically detectable definition pattern of a label which is attached to a respective reagent container carrier structure being placed in a corresponding compartment just below the reader module 90 at the respective stop position of the reagent rotor. In case that the compartments of both lanes of the reagent rotor, i.e. those of the inner lane and those of the outer lane can be fully occupied by reagent container carrier structures, the reader module 90 could read, by means of its two RFID readers 92 and the respective arrangement of the optical elements 94, the RFID data and the optically detectable data of the labels of the reagent container carrier structures of the inner lane as well as those of the outer lane. By means of the RFID data and the optically detectable definition pattern which should be present in the case that a reagent container carrier structure is placed within a corresponding compartment of the conveyor system, it is possible to detect whether a reagent container carrier structure is actually present or not within a respective compartment of the reagent rotor. Furthermore, it is possible to detect whether a reagent container carrier structure is in the right orientation with respect to the reagent rotor when the respective reagent container carrier structure is provided with an orientation identification label comprising an optically detectable definition pattern according to the invention and as further outlined, for example, with reference to FIGS. 1a, 1b and 2. With reference to one label, the information (data) of the optical elements 94 and the RFID data received via the RFID reader 92 can be transferred to an analysis unit either together in one data protocol or independently of each other. Particularly, in the case that the optical data and the RFID data are transferred independently of each other, it is helpful, if the RFID data and the data read by the optical elements are read nearly simultaneously so that the mutual assignment of the different data is facilitated.

Furthermore, it is possible that each or at least a part of the optical elements 94 provide a LED light source, since it is mostly dark within a housing of a reagent rotor. Alternatively, it is also possible that the optical elements or at least a part of the optical elements provide an integrated light source.

A similar arrangement of a reader module 90 is possible in case of a so-called one-lane reagent rotor, whereby the reader module 90 comprises only one RFID reader 92 and a respective pair of optical elements 94 which are symmetrically arranged to each other with respect to the RFID reader 92.

According to the invention, it is also possible that there is only one optical element or a plurality of optical elements which are appropriately arranged with respect to the RFID reader. Furthermore, it is possible that the optical element is provided as an array of optical sensors or as a CCD chip.

Moreover, it is possible that in dependence on the light circumstances a special light source is provided, such as a LED light source or a point source.

Otherwise, it is also possible to provide a diffuse light source. The optical elements are to be chosen appropriately, i.e. in dependency on the light source.

In case that the reagent rotor or another provided type of reagent housing in use has to be cooled, it can be required to protect the optical elements against condensed water which can be realized by providing appropriate housings for the optical elements. Alternatively, it would also be possible to provide appropriate seals in order to protect the optical elements. The optical elements can also be placed behind heated windows.

It is also possible that the RFID data and the optically detectable data of a label are read by the reader module 90 "on the fly", i.e. without stopping a respective conveyor system, e.g. a reagent rotor during its rotation. In that case, the reader module 90 does not pause on top of a respective reagent container carrier structure which is located within a compartment of the conveyor system, for reading out the respective data. In that case, the conveyance velocity of the conveyor system is to be adapted to the readout period which is required by the reader module 90 to read the respective data. The readout period can be generally set to about 200 ms.

In case that the labels are to be read "on the fly" it can be advantageous with reference to FIG. 6, for example, to turn each label on the reagent containers about 90°, respectively, so that it seems to the reader module, in case that all containers are placed in the right direction within the reagent rotor, that there are two continuous lanes, i.e. a white lane and a black lane, respectively, which are to be read. Thus, a wrongly placed container, i.e. a container which is placed in a wrong direction, can be easily identified.

The optical elements 94 and the RFID reader 92 can be mounted either on one common board or on different boards.

However, in view of the required local vicinity of a respective RFID reader 92 and a corresponding pair of optical elements 94 according to the proposed geometry of FIG. 10, it can be advantageous to provide one common board for both, a respective RFID reader 92 and the corresponding pair of optical elements 94 assignable to it.

Figure 11:
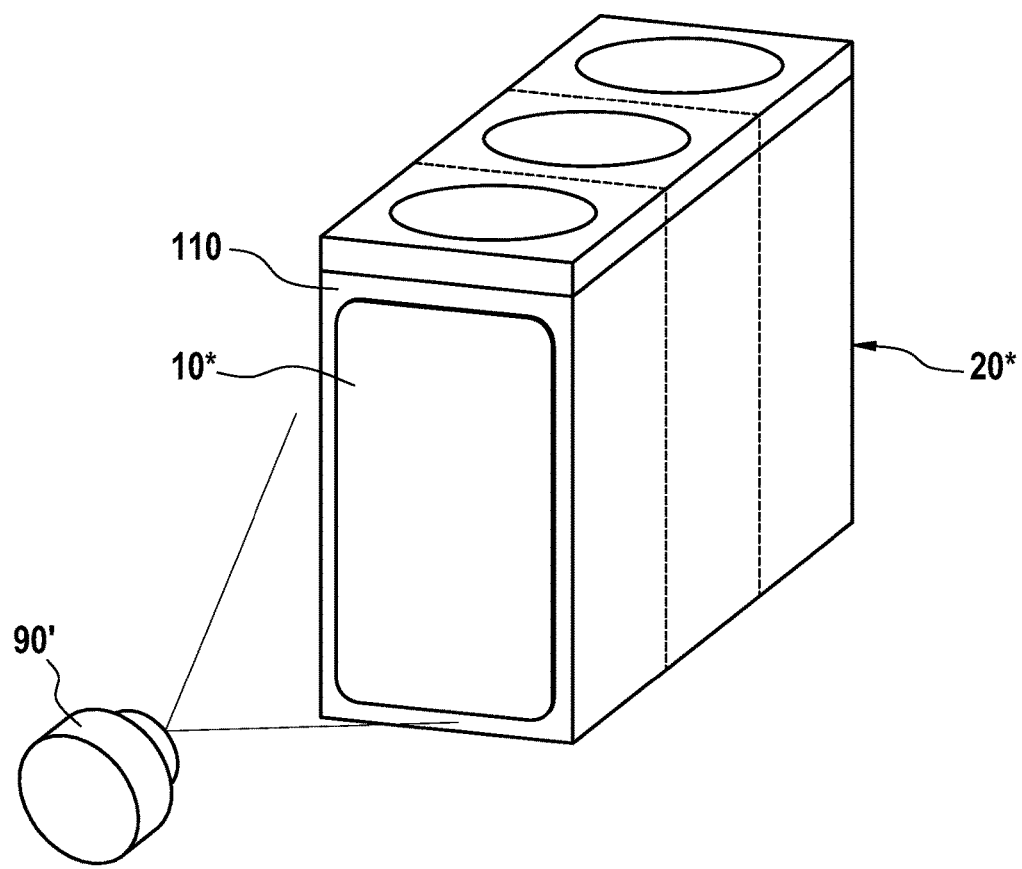
FIG. 11 shows in highly schematic manner a third embodiment of a reagent container carrier structure with an alternative location of the orientation identification label of the invention.

FIG. 11 shows a further embodiment of a reagent container carrier structure according to the invention. The reagent container carrier structure 20* shown in FIG. 11 is illustrated in highly schematic manner, leaving out details that have been shown and explained in detail with reference to FIG. 3. The reagent container carrier structure 20* of FIG. 11 is very similar in appearance to the container structure of FIG. 3. The depiction of FIG. 11 illustrates an alternative manner of applying the orientation identification label 10* according to the present invention, namely at a side surface 110 of the reagent container carrier structure 20* or around an edge between two surfaces, namely a side surface and a top surface. This would allow to read the label 10* optically and electronically from sideways with regard to the reagent container carrier structure 20*. This would allow locating the reader module 90' sideways with regard to a conveyor system holding reagent container carrier structures to be analyzed. This would also allow to provide only one label 10*, namely on a side surface of a respective reagent container carrier structure 20* instead of two labels, one on the top surface and a further one on a side surface of the reagent container carrier structure 20*.

In case that the basic color of the label 10* differs from the color of the reagent container carrier structure 20*, it would be possible to leave a defined detection part of the label 10* in this basic color which would be sufficient for that a reader module 90' according to the invention can detect by means of its at least one optical element whether a reagent container carrier structure 20* is present, and, moreover, whether the reagent container carrier structure 20* is correctly placed within the respective conveyor system. Generally said, the optically detectable definition pattern of label 10* can be designed in one color which is silhouetted against the color of the reagent container carrier structure 20*.

In the case, for example, that the reagent container carrier structure 20* is "black" and the label's basic color is "white", the following exemplary-scenarios can be detected.

The reader module detects "white" via its at least one optical element and a RFID signal via its RFID reader, thus indicating that the reagent container carrier structure is in a correct position. The reader module detects "white" but no RFID signal, thus indicating that a reagent container carrier structure is present, but the RFID data of the respective label is not readable. The reader module detects "black", thus indicating that a reagent container carrier structure is present, but that the reagent container carrier structure is inserted in a wrong position, e.g. in a wrong direction.

In case that the reader module, i.e. its at least one optical element is configured to differentiate between "black", "white", and "no reflection surface", the reader module can also detect if a reagent container carrier structure is missing.

Instead of "black" for the reagent container carrier structure and "white" for the label's basic color, a variety of further color combinations can be chosen. The reagent container carrier structure can be, for example, transparent or nearly transparent and the label's color "white", "black", or any other appropriate color. If the basic color of the label is not appropriate, the label's detection part, i.e. its optically detectable definition pattern can also be printed appropriately.

Figure 12:
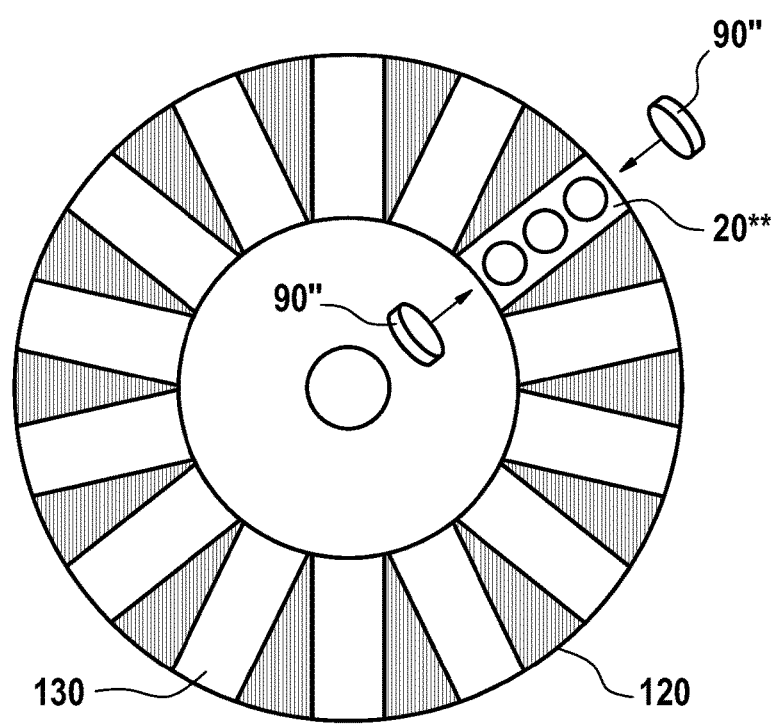
FIG. 12 shows in highly schematic manner an exemplary embodiment of a rotary conveyor system of an analyzer device for analyzing chemical, biological or pharmaceutical work probes with one reagent container carrier structure according to the invention placed therein.

In the case of a rotor 120 as conveyor system, the reader module 90" can be positioned, as indicated in FIG. 12 by arrows, respectively, in the central part of the rotor 120 or at an appropriate position outside at the circumference of the rotor 120.

In both cases, the reader module 90" is placed sideways with respect to any compartment 130 of the rotor 120, the compartments 130 being destined to hold reagent container carrier structures as indicated by an exemplary reagent container carrier structure 20**.

What is claimed is:

1. A carrier structure for holding at least one reagent container, the carrier structure comprising an RFID assembly and an optically detectable definition pattern defining a presence and an orientation of the carrier structure for holding at least one reagent container, the RFID assembly comprising an RFID chip and an RFID antenna, the optically detectable definition pattern consisting of a geometrical design in contrastive colors and readable by an optical detection device and by a human operator.

2. The carrier structure according to claim 1, wherein the geometrical design is asymmetric to an axis of the design which is substantially perpendicular to the direction of orientation to be identified and not point-symmetric.

3. The carrier structure according to claim 1 further comprising a single label having a front and a back, the back being attached to the reagent container carrier structure, the label including the RFID assembly and the optically detectable definition pattern.

4. The carrier structure according to claim 3, wherein the optically detectable definition pattern is on the front of the label and the RFID assembly is on the back of the label.

5. The carrier structure according to claim 4 in which the label is attached to the carrier structure by adhesive on the back of the label.

6. The carrier structure according to claim 1 further comprising first and second labels attached to the carrier structure, the first label including the RFID assembly and the second label including the optically detectable definition pattern.

7. The carrier structure according to claim 6, wherein one of the first and second labels comprises a lower label attached directly to the carrier structure, and the other of the first and second labels comprises an upper label attached on top of the lower label.

8. A carrier structure for holding at least one reagent container, the carrier structure comprising an RFID assembly and an optically detectable definition pattern defining a presence and an orientation of the carrier structure for holding at least one reagent container, the optically detectable definition pattern consisting of a geometrical design in contrastive colors and readable by an optical detection device and by a human operator, the pattern comprising at least two different sub-patterns allowing identification of an orientation of the reagent container carrier structure.

9. The carrier structure according to claim 8 further comprising a single label having a front and a back, the back being attached to the reagent container carrier structure, the label including the RFID assembly and the optically detectable definition pattern.

10. The carrier structure according to claim 9, wherein the optically detectable definition pattern is on the front of the label and the RFID assembly is on the back of the label.

11. The carrier structure according to claim 8 further comprising first and second labels attached to the carrier structure, the first label including the RFID assembly and the second label including the optically detectable definition pattern.

12. The carrier structure according to claim 11, wherein one of the first and second labels comprises a lower label attached directly to the reagent container carrier structure, and the other of the first and second labels comprises an upper label attached on top of the lower label.

13. The carrier structure according to claim 8, wherein the geometrical design is asymmetric to an axis of the design which is substantially perpendicular to the direction of orientation to be identified and not point-symmetric.

14. A carrier structure for holding at least one reagent container, the carrier structure comprising an RFID assembly and an optically detectable definition pattern defining a presence and an orientation of the carrier structure for holding at least one reagent container, the optically detectable definition pattern consisting of a geometrical design in contrastive colors and readable by an optical detection device and by a human operator, the geometrical design being asymmetric to at least one of the transversal and longitudinal axes of the carrier structure and not point-symmetric.

15. The carrier structure according to claim 14, wherein the geometrical design is asymmetric to an axis of the design which is substantially perpendicular to the direction of orientation to be identified and not point-symmetric.

16. The carrier structure according to claim 14 further comprising a single label having a front and a back, the back being attached to the reagent container carrier structure, the label including the RFID assembly and the optically detectable definition pattern.

17. The carrier structure according to claim 16, wherein the optically detectable definition pattern is on the front of the label and the RFID assembly is on the back of the label.

18. The carrier structure according to claim 14 in which the label is attached to the carrier structure by adhesive on the back of the label.

19. The carder structure according to claim 14 further comprising first and second labels attached to the carrier structure, the first label including the RFID assembly and the second label including the optically detectable definition pattern.

20. The carrier structure according to claim 19, wherein one of the first and second labels comprises a lower label attached directly to the carrier structure, and the other of the first and second labels comprises an upper label attached on top of the lower label.

* * * * *